US006726319B1

United States Patent
Yanase et al.

(10) Patent No.: US 6,726,319 B1
(45) Date of Patent: Apr. 27, 2004

(54) METHOD FOR INSPECTING SURFACE OF SEMICONDUCTOR WAFER

(75) Inventors: Yoshio Yanase, Fujitsu-gun (JP); Osamu Nakamura, Katori-gun (JP); Takashi Koike, Imari (JP); Noboru Kudo, Ashiya (JP)

(73) Assignee: Sumitomo Mitsubishi Silicon Corporation, Tokyo (JP)

( * ) Notice: Subject to any disclaimer, the term of this patent is extended or adjusted under 35 U.S.C. 154(b) by 20 days.

(21) Appl. No.: 09/856,982

(22) PCT Filed: Oct. 13, 2000

(86) PCT No.: PCT/JP00/07147
§ 371 (c)(1),
(2), (4) Date: May 30, 2001

(87) PCT Pub. No.: WO01/27600
PCT Pub. Date: Apr. 19, 2001

(30) Foreign Application Priority Data

Oct. 14, 1999 (JP) ............................................. 11-291968

(51) Int. Cl.$^7$ ............................................... G01N 21/00
(52) U.S. Cl. ............................... 356/237.4; 356/237.1; 250/559.27
(58) Field of Search .......................... 356/237.1, 237.2, 356/237.3, 237.4, 237.5, 237.6, 601, 614, 388, 392, 393, 394; 250/559.27, 559.31, 559.41, 559.18

(56) References Cited

U.S. PATENT DOCUMENTS

| 4,902,131 A | * | 2/1990 | Yamazaki et al. ........ 356/237.1 |
| 6,115,117 A | * | 9/2000 | Isozaki .................... 356/237.4 |
| 6,256,093 B1 | * | 7/2001 | Ravid et al. ............. 356/237.2 |
| 6,292,259 B1 | * | 9/2001 | Fossey et al. ........... 356/237.2 |

FOREIGN PATENT DOCUMENTS

| JP | 11-501727 | 2/1999 |
| JP | 11-64234 | 3/1999 |
| JP | 11-111792 | 4/1999 |
| JP | 2000-162141 | 6/2000 |
| WO | 98/25131 | 6/1998 |

* cited by examiner

Primary Examiner—Frank G. Font
Assistant Examiner—Sang Hoang Nguyen
(74) Attorney, Agent, or Firm—Wenderoth, Lind & Ponack, L.L.P.

(57) ABSTRACT

Particles adherent to a semiconductor wafer surface, and defects such as SFs, mounds, and dislocations present near the semiconductor wafer surface can be accurately divided according to their types at a low cost without being influenced by an inspector's ability. The wafer is scanned with a laser beam, scattered or reflected light from the wafer surface is detected from multiple light optics having different detecting angles, respectively, and forms and types of the occurrences present on the wafer surface are determined based on a ratio of detected light intensities from the multiple light optics.

25 Claims, 7 Drawing Sheets

METHOD FOR INSPECTING SURFACE OF SEMICONDUCTOR WAFER

TECHNICAL FIELD

The present invention relates to a method for inspecting a semiconductor wafer surface and, more particularly, to a method for inspecting a semiconductor wafer surface for dividing, to detect according to types of defects present on and near a semiconductor wafer surface, particles adherent to the semiconductor wafer surface and the like (hereinafter referred to as occurrences associated with the semiconductor wafer), which affect electrical properties such as dielectric breakdown strength of LSIs and the like being manufactured using semiconductor wafers, so as to evaluate semiconductor wafer quality.

BACKGROUND ART

Hitherto, extraneous substances such as particles adherent on a semiconductor wafer, and crystal defects on and near a surface of the semiconductor wafer, or surface flaws, scratches, shallow pits and the like (hereinafter referred to as surface flaws) have been known as light point defects (LPDs) to be detected using a semiconductor wafer surface inspection apparatus. The extraneous substances are observed in a shape of a convex on the semiconductor wafer surface. The crystal defects are observed mainly as a quadrangular-pyramidal pit or projection [(100) wafer], or a triangular or hexagonal pit or projection [(111) wafer] on a mirror-finished wafer surface, while these defects are observed mainly in a shape of a square or a square that is partly concave or convex [(100) wafer], or in a shape of a triangle or a triangle that is partly concave or convex [(111) wafer] on an epitaxial wafer surface.

From a viewpoint of evaluation of semiconductor wafer quality, it is desirable that the extraneous substances, crystal defects and surface flaws be strictly divided according to their types to be detected. However, in a conventional method for inspecting a semiconductor wafer surface, a wafer is scanned with a laser beam, a scattered light having a prescribed angle reflected from the wafer surface is detected, and a result is compared with measurement results of standard particles having prescribed grain sizes previously obtained, whereby the number of LPDs of every size including all of the extraneous substances and crystal defects is obtained.

In order to determine the types of extraneous substances and crystal defects or surface flaws (hereinafter referred to as defects) in the above method, a possibility of separation by unevenness recognition based on a premise that grown-in defects are pit-shaped while particles are convex, for example, in separation of particles and grown-in defects (COPs) in a mirror-finished wafer was reported. However, since the unevenness recognition is actually imperfect, it has been evident that it is difficult to separate particles from grown-in defects (COPs). In addition, it has been evident that all of grown-in defects are not concave.

There are many types of crystal defects in an epitaxial wafer such as stacking faults (SFs), mounds, and dislocations (hereinafter referred to as epi defects), and some of the epi defects have concave shapes, some have convex shapes, and others have both concave and convex shapes. Therefore, since separation probability in a method wherein separation is conducted depending on concave and convex shapes is low, and all of the epi defects are not concave, it has been physically impossible to separate the epi defects from particles; moreover, to determine types of the defects.

Determination of the types of occurrences associated with the semiconductor wafer is possible using an atomic force microscope (AFM) or a scanning electron microscope on a research level. However, in order to observe these occurrences using these microscopes, coordinate positions where the occurrences exist must be detected first on a wafer surface having an enormously large area compared with the occurrences. This detecting activity is very difficult, and then, points where the occurrences exist must be brought into focus of the AFM or scanning electron microscope. These activities cost vast labor and time, and furthermore, there is a possibility that quality of a product might be lowered, even though inspection techniques used are not destructive. As a result, it has been actually impossible to conduct inspection using a microscope of this type on every product. Therefore, a visual distinction method performed by an inspector (a method wherein a high-intensity spotlight is irradiated in a darkroom and scatterers are detected by a visual check) has been actually adopted.

An occurrence size measured using only one light optic of a laser surface inspection apparatus is a standard particle conversion size, which may be very different from an actual size depending on shapes of the occurrences associated with the semiconductor wafer. Accordingly, a problem remains from a viewpoint of reliability with regard to distinction of types of the occurrences based on size of the occurrences. Not only does the method, wherein particles and defects are separated by judging whether shapes are concave or convex, have a low reliability, but also it cannot be applied at all to wafers wherein convex defects exist. In the visual distinction method performed by an inspector, distinction capacity greatly depends on the inspector's competence for the task, which is not stable, and it is difficult to respond to higher-level requirements in a future wafer inspection. Furthermore, as wafers have larger diameters, possibility that occurrences escape the inspectors attention becomes larger. In the visual distinction method performed by an inspector, ability of the inspector must be estimated first, leading to increases in the number of steps and costs.

SUMMARY OF THE INVENTION

The present invention was developed in order to solve the above problems, and it is an object to provide a method for inspecting a semiconductor wafer surface, wherein particles adherent to a semiconductor wafer surface and, for example, surface flaws in a mirror-finished wafer which exist near the semiconductor wafer surface, or grown-in defects in bulk near the surface can be separated to be detected, or adherent particles and defects such as SFs, mounds, and dislocations in an epitaxial wafer can be accurately divided according to types at a low cost, without being influenced by an inspector's ability.

In order to achieve the above object, a first method for inspecting a semiconductor wafer surface according to the present invention is characterized by a wafer being scanned with a laser beam, scattered or reflected light from the wafer surface being detected by multiple light optics having different detecting angles relative to an incident light, respectively, and an occurrence being classified into some characteristics based on the ratio of the detected light intensities from the multiple light optics.

In the above first method for inspecting a semiconductor wafer surface, since a wafer is scanned with a laser beam, scattered or reflected light from the wafer surface is detected by multiple light optics having different detecting angles relative to an incident light, respectively, and the occurrence is classified into some characteristics based on the ratio of the detected light intensities from the multiple light optics, the method can be utilized when there is a wide difference in detected defect sizes between a low-angle light optic and a high-angle light optic depending on types of the occurrences. Therefore, it becomes possible to quite accurately determine the types of the occurrences. Since determination is not conducted by an inspector, inspection can be automated. Without depending on an inspector's ability, the inspection can be stable and it is possible to deal with higher-level requirements in a future wafer inspection and with wafers having larger diameters. Moreover, it is unnecessary to estimate an inspector beforehand, leading to substantial reductions in the number of inspection steps and costs.

A second method for inspecting a semiconductor wafer surface according to the present invention is characterized by a wafer being scanned with a laser beam, scattered or reflected light from the wafer surface being detected by multiple light optics having different detecting angles relative to an incident light, respectively, a difference between a horizontal length and a vertical height or between a horizontal length and a horizontal length crossing at right angles (i.e. orthogonal dimensions) of an LPD (Light Point Defect) present on the wafer surface being calculated from a difference in standard particle conversion sizes based on a ratio of detected light intensities from the multiple light optics, and forms (i.e. shapes) and types of occurrences present on the wafer surface are determined.

In the above second method for inspecting a semiconductor wafer surface, since a wafer is scanned with a laser beam, scattered or reflected light from the wafer surface is detected by multiple light optics having different detecting angles relative to an incident light, respectively, a difference between a horizontal length and a vertical height or two orthogonal lengths of an LPD (Light Point Defect) present on and near the wafer surface is calculated from a difference in the standard particle conversion sizes based on the ratio of the detected light intensities from the multiple light optics, and the forms (i.e. shapes) and types of defects present on the wafer surface are determined, it is possible to distinctly separate the defects from extraneous substances. Furthermore, it becomes possible to quite accurately determine the types of the defects. Since determination is not conducted by an inspector, inspection can be automated. Without depending on an inspector's ability, the inspection can be stable and it is possible to deal with higher-level requirements in a future wafer inspection and also with wafers having larger diameters. Moreover, it is unnecessary to estimate an inspector beforehand, leading to substantial reductions in the number of inspection steps and costs.

A third method for inspecting a semiconductor wafer surface according to the present invention is characterized by using a laser surface inspection apparatus, comprising at least two light optics to one incidence, as a laser surface inspection apparatus in the first or second method for inspecting a semiconductor wafer surface.

When at least two light optics, a low-angle light optic and a high-angle light optic, relative to an incident light are included as a light-detecting system of the laser surface inspection apparatus, the above first and second methods for inspecting a semiconductor wafer surface can be performed. By using a laser surface inspection apparatus comprising two light optics relative to one incidence as a laser surface inspection apparatus, inspection costs can be held down.

A fourth method for inspecting a semiconductor wafer surface according to the present invention is characterized by the semiconductor wafer being an epitaxial semiconductor wafer in any of the first through third methods for inspecting a semiconductor wafer surface.

By the methods for inspecting a semiconductor wafer surface according to the present invention, it is possible to accurately determine types of occurrences present on the wafer surface. Therefore, the methods can be applied even to an epitaxial semiconductor wafer which has many types of occurrences and a small number of occurrences.

A fifth method for inspecting a semiconductor wafer surface according to the present invention is characterized by determining forms (i.e. shapes) and types of occurrences according to a combination of A, B and a numerical value given by A/B, where detected light intensity of an LPD (Light Point Defect) detected from a high-angle light optic, or standard particle conversion size thereof, is A, while detected light intensity of the LPD detected from a low-angle light optic, or standard particle conversion size thereof, is B, in any of the first through fourth methods for inspecting a semiconductor wafer surface.

Using the above fifth method for inspecting a semiconductor wafer surface, particles adherent to a semiconductor wafer surface, or defects such as SFs, mounds, and dislocations present near the semiconductor wafer surface can be accurately classified, so that semiconductor wafer quality can be accurately evaluated.

A sixth method for inspecting a semiconductor wafer surface according to the present invention is characterized by determining forms (i.e. shapes) and types of occurrences based on Table 1, where standard particle conversion size of an LPD (Light Point Defect) detected in a high-angle light optic is A, while the standard particle conversion size of the LPD detected from a low-angle light optic is B, in any of the first through fourth methods for inspecting a semiconductor wafer surface.

TABLE 1

| Relations between A and B or ranges | Actual types |
| --- | --- |
| A ≧ B × 1.13 | Stacking Fault |
| A < B × 1.13 | Non-epi-layer originated extraneous substance (adherent particle) |
| B < 90 nm and A > 107 nm | Micro-crystallographic-defect (hillock, shadow, dislocation) |
| B > 160 nm and A < 107 nm | Abnormal growth (large-pit, projection) |
| Others | Abnormal product |

Using the above sixth method for inspecting a semiconductor wafer surface, particles adherent to a semiconductor wafer surface, or defects such as SFs, mounds, and dislocations present near the semiconductor wafer surface can be accurately classified, so that semiconductor wafer quality can be accurately evaluated.

A seventh method for inspecting a semiconductor wafer surface according to the present invention is characterized by the semiconductor wafer being a mirror-finished semiconductor wafer in any of the first through third methods for inspecting a semiconductor wafer surface.

By the first through third methods for inspecting a semiconductor wafer surface according to the present invention, occurrences present on the wafer surface, and surface flaws and grown-in defects in bulk near the surface can be accurately separated. Therefore, these methods can be applied even to a mirror-polished semiconductor wafer.

An eighth method for inspecting a semiconductor wafer surface according to the present invention is characterized by determining forms (i.e. shapes) and types of occurrences according to a combination of A, B and a numerical value given by A/B, where detected light intensity of an LPD (Light Point Defect) detected from a high-angle light optic, or standard particle conversion size thereof, is A, while detected light intensity of the LPD detected from a low-angle light optic, or standard particle conversion size thereof, is B, in the seventh method for inspecting a semiconductor wafer surface.

Using the above eighth method for inspecting a semiconductor wafer surface, particles adherent to a semiconductor wafer surface or COPs, and surface flaws and grown-in defects present in bulk near the semiconductor wafer surface can be accurately classified, so that semiconductor wafer quality can be accurately evaluated.

A ninth method for inspecting a semiconductor wafer surface (9) according to the present invention is characterized by determining forms (i.e. shapes) and types of occurrences based on Table 2, where standard particle conversion size of an LPD (Light Point Defect) detected from a high-angle light optic is A, while standard particle conversion size of the LPD detected from a low-angle light optic is B, in any of the first through third and seventh methods for inspecting a semiconductor wafer surface.

TABLE 2

| Relations between A and B or ranges | Actual types |
| --- | --- |
| A ≧ b × 1.13 or B < 90 nm and A > 107 nm | Scratch, flaw, and shallow pit |
| A < B × 1.13 B ≧ 85 nm and A < 107 nm | Adherent particle or COP Grown-in defect in bulk near surface |

Using the above ninth method for inspecting a semiconductor wafer surface, particles adherent to a semiconductor wafer surface or COPs, and surface flaws and grown-in defects present in bulk near the semiconductor wafer surface can be accurately classified, so that semiconductor wafer quality can be accurately evaluated.

DESCRIPTION OF THE PREFERRED EMBODIMENTS

Figure 1:
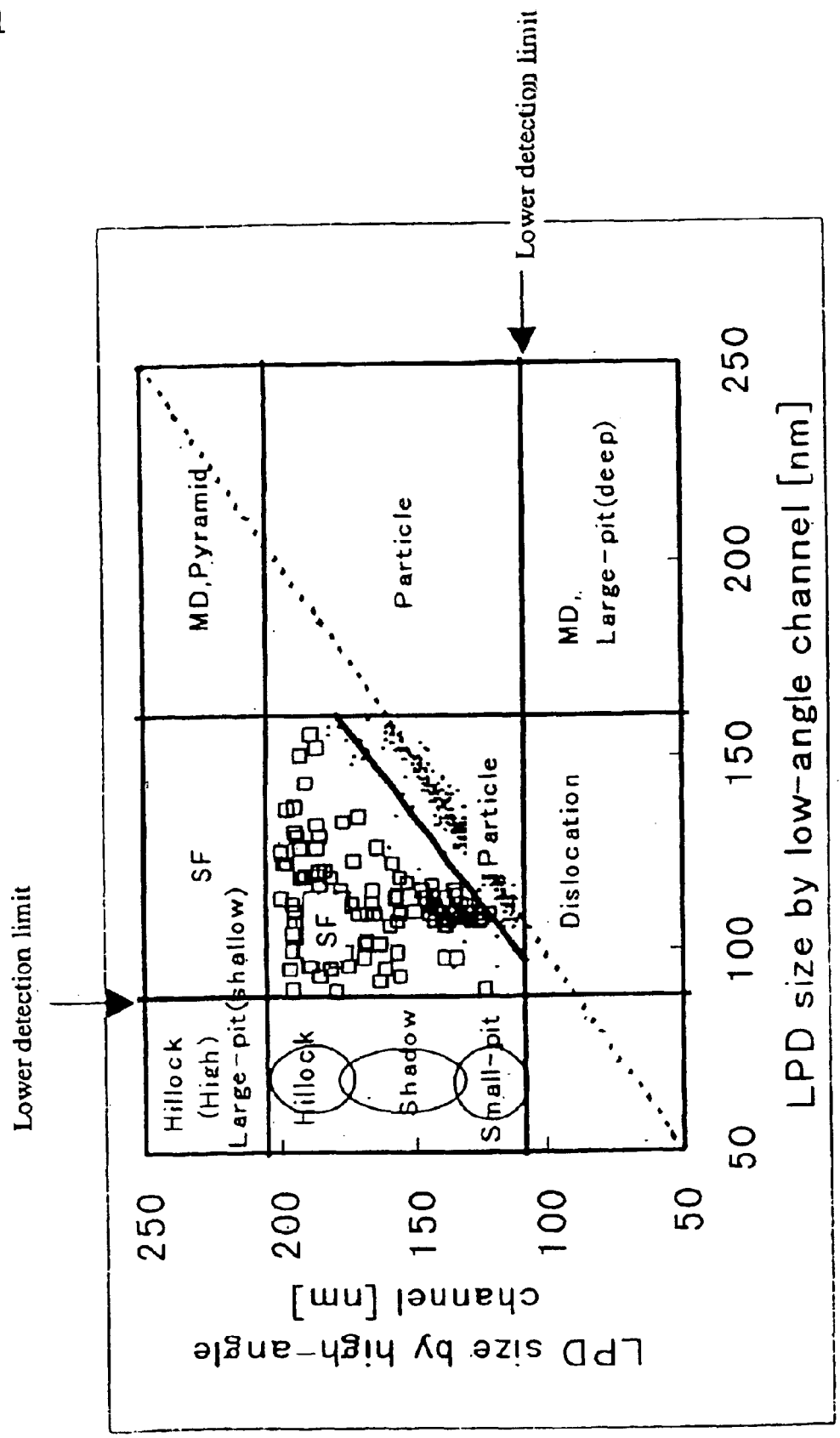
FIG. 1 is a diagram showing results of classification of actual forms of LPDs detected in a first embodiment according to the present invention after confirmed using an AFM.

The preferred embodiments of a method for inspecting a semiconductor wafer surface according to the present invention are described below by reference to the Figures of the Drawings.

In a method for inspecting a semiconductor wafer surface according to an embodiment, using, for example, a laser surface inspection apparatus having two light optics relative to one incidence, LPDs are detected from the two light optics, i.e. a low-angle one and a high-angle one. A list of coordinates of the LPDs obtained from each light optic, detected light intensity or standard particle conversion size data thereof, and (high-angle detected light intensity or standard particle conversion size/low-angle detected light intensity or standard particle conversion size) is prepared.

The LPDs detected only from the high-angle light optic, the LPDs detected only from the low-angle light optic, and the LPDs having various values of (high-angle detected light intensity or standard particle conversion size/low-angle detected light intensity or standard particle conversion size) are selected and actual forms thereof are actually observed using an AFM or the like.

On the basis of the actual forms of the LPDs observed using the AFM or the like, characteristics of occurrences associated with the semiconductor wafer are grasped according to their types from comparison between detected light intensities or standard particle conversion sizes detected from each of the low-angle and high-angle light optics. As a result, for example, relationships between the standard particle conversion sizes detected from each of the low-angle and high-angle light optics and types of defects in an epitaxial wafer and in a mirror-finished wafer could be classified and arranged as shown in Tables 1 and 2, respectively.

TABLE 1

| Relations between A and B or ranges | Actual types |
| --- | --- |
| A ≧ B × 1.13 | Stacking Fault |
| A < B × 1.13 | Non-epi-layer originated extraneous substance (adherent particle) |
| B < 90 nm and A > 107 nm | Microcrystallographic-defect (hillock, shadow, dislocation) |
| B > 160 nm and A < 107 nm | Abnormal growth (large-pit, projection) |
| Others | Abnormal product |

TABLE 2

| Relations between A and B or ranges | Actual types |
|---|---|
| A ≧ B × 1.13 or B < 90 nm and A > 107 nm | Scratch, flaw, and shallow pit |
| A < B × 1.13 B ≧ 85 nm and A < 107 nm | Adherent particle or COP Grown-in defect bulk near surface |

Here, A represents the standard particle conversion size of an LPD detected from the high-angle light optic, while B represents the standard particle conversion size of an LPD detected from the low-angle light optic.

However, angles of the light optics are different depending on a used laser surface inspection apparatus, and each laser surface inspection apparatus has its own minimum and maximum limits of measurement. Therefore, there is a possibility that the values of A, B, and A/B used for defect distinction might vary according to the used laser surface inspection apparatus. In addition, in the case of an epitaxial wafer, an occurrence size depends on thickness of an epitaxial film (in the case of a (100) wafer, SF length is about 1.4 times the epitaxial film thickness), so that there is a possibility that the values of A, B, and A/B might vary when the epitaxial film thickness varies.

By a conventional method, in the case of an epitaxial wafer, the number of LPDs of every size from one light optic, including all of extraneous substances and epi defects detected using a laser surface inspection apparatus, can be obtained; while in the case of a mirror-polished wafer, the number of LPDs of every size from one light optic, including all of extraneous substances and grown-in defects detected using a laser surface inspection apparatus, can be obtained. However, it is impossible to divide and detect occurrences associated with the semiconductor wafer according to the types as shown in Tables 1 or 2.

An occurrence size measured using only one light optic of a laser surface inspection apparatus is a standard particle conversion size, which may be very different from an actual size depending on shapes of the occurrences. Accordingly, a problem remains from the viewpoint of reliability with regard to distinction of types of the occurrences, based on the occurrence size. In a visual distinction method by an inspector, distinction capacity greatly depends on the inspector's competence for the task, which is not stable, and it is difficult to respond to higher-level requirements in a future wafer inspection. Furthermore, as wafers have larger diameters, a possibility that occurrences escape his attention becomes larger. In the visual distinction method by an inspector, ability of the inspector must be estimated first, leading to increases in the number of steps and costs.

In the method for inspecting a semiconductor wafer surface according to the embodiment, on the basis of the coordinate data of the LPDs detected using the laser surface inspection apparatus, the LPDs detected only in the high-angle light optic, the LPDs detected only in the low-angle light optic, and the LPDs having various values of (high-angle detected light intensity or standard particle conversion size/low-angle detected light intensity or standard particle conversion size) are selected. On the basis of results of the actual forms thereof actually observed using an AFM, the LPDs are classified and arranged to prepare Tables 1 and 2. Once Table 1 or 2 is prepared, only organization of the standard particle conversion sizes detected from each of the low-angle and high-angle light optics, using the laser surface inspection apparatus, according to the classification shown in Table 1 or 2 is needed to divide easily and accurately extraneous substances and defects, or surface flaws according to their types.

Since the distinction is not conducted by an inspector, the inspection can be automated, so that it can be stably conducted without depending on the inspector's ability. It is also possible to deal with higher-level requirements in a future wafer inspection, and wafers having larger diameters. Moreover, it is unnecessary to estimate the inspector beforehand, leading to substantial reductions in the number of inspection steps and costs.

In the method for inspecting a semiconductor wafer surface according to the embodiment, a laser surface inspection apparatus having two light optics relative to one incidence is used, but the laser surface inspection apparatus is not so limited. In another embodiment, a laser surface inspection apparatus having two light optics relative to two incidences, or a laser surface inspection apparatus having three light optics relative to one incidence, can be used.

When the laser surface inspection apparatus has at least two light optics having different detecting angles relative to an incident light, as a light-detecting system thereof, it is possible to conduct a method for inspecting a semiconductor wafer surface according to the present invention. And, using a laser surface inspection apparatus having two light optics relative to one incidence, inspection costs can be held down.

By the method for inspecting a semiconductor wafer surface according to the embodiment, types of occurrences present on a wafer surface can be accurately determined, so that the method can be applied not only to detection of surface flaws of a mirror-polished semiconductor wafer sliced off from a single crystal, but also to an epitaxial semiconductor wafer having many types of occurrences and a small number of occurrences. Quality evaluation of both an epitaxial semiconductor wafer having many types of occurrences and a mirror-polished wafer can be accurately conducted.

EXAMPLES AND COMPARATIVE EXAMPLES

Examples of the method for inspecting a semiconductor wafer surface according to the present invention are described below.

Example 1

Used laser surface inspection apparatus: SP-1 (produced by TENCOR)
  Two light optics relative to one incidence
Used sample: 200 mm epitaxial silicon wafer
  Wafer crystal plane (100)
  Epitaxial film thickness 6 μm
LPDs of the sample epitaxial silicon wafer were detected using the above laser surface inspection apparatus.

Data of coordinates and standard particle conversion sizes of the LPDs obtained from each of the two light optics were organized, and actual forms of the LPD were presumed based on classification shown in Table 1 and FIG. 1. A portion of results of data processing is shown in Table 3.

TABLE 3

Detection results by laser surface inspection apparatus

Figure 2:
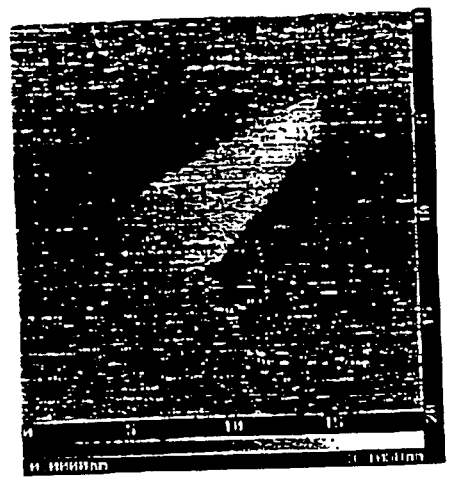
FIG. 2 is a microphotograph showing an example of actual forms of LPDs detected in the first embodiment, which were confirmed using the AFM.
Figure 3:
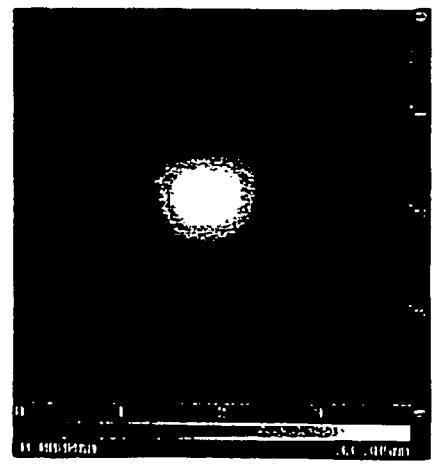
FIG. 3 is a microphotograph showing an example of actual forms of LPDs detected in the first embodiment, which were confirmed using the AFM.
Figure 4:
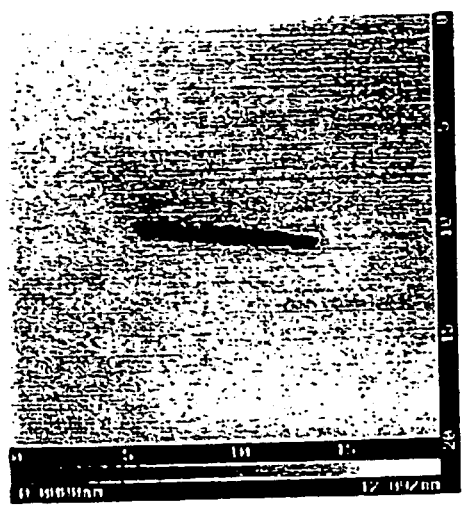
FIG. 4 is a microphotograph showing an example of actual forms of LPDs detected in the first embodiment, which were confirmed using the AFM.
Figure 5:
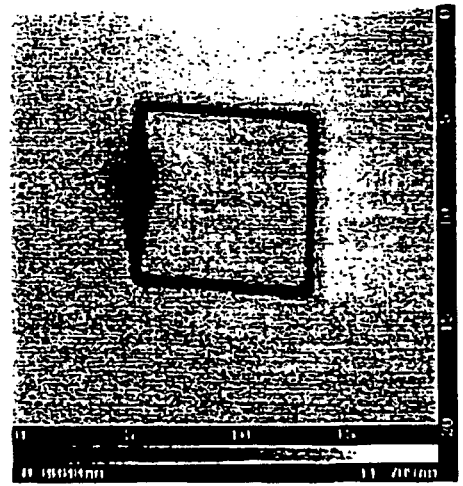
FIG. 5 is a microphotograph showing an example of actual forms of LPDs detected in the embodiment, which were confirmed using the AFM.
Figure 6:
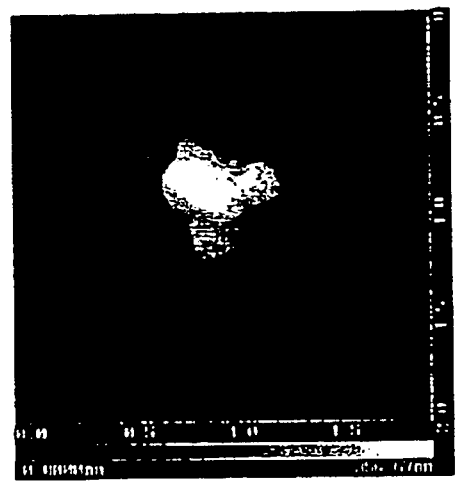
FIG. 6 is a microphotograph showing an example of actual forms of LPDs detected in the first embodiment, which were confirmed using the AFM.
Figure 7:
FIG. 7 is a microphotograph showing an example of actual forms of LPDs detected in the first embodiment, which were confirmed using the AFM.

| Low-angle light-receiving channel (nm) | High-angle light-receiving channel (nm) | Presumption | AFM | Results |
|---|---|---|---|---|
| Below detection limit | 115 | Micro-crystallographic-defect (dislocation, shadow) | Length 10 μm · height 3 nm (FIG. 2) | ○ |
| Below detection limit | 160 | Micro-crystallographic-defect (hillock) | Diameter 1 μm × height 20 nm (FIG. 3) | ○ |
| 95 | 127 | S F | S F (FIG. 4) | ○ |
| 108 | 136 | S F | S F (FIG. 5) | ○ |
| 106 | 136 | S F | S F | ○ |
| 107 | 135 | S F | S F | ○ |
| 107 | 134 | S F | S F | ○ |
| 149 | 150 | Adherent particle | Adherent particle (FIG. 6) | ○ |
| 104 | 111 | Adherent particle | Adherent particle | ○ |
| 90 | 118 | S F | S F | ○ |
| Above detection limit | Above detection limit | Mound | Mound · abnormal growth (FIG. 7) | ○ |

Then, on the basis of the coordinate data of the obtained LPDs, actual forms of the LPDs detected using the laser surface inspection apparatus were actually confirmed using an AFM, and whether the classification based on Table 1 and FIG. 1 was correct or wrong was judged. The results are also shown together in Table 3.

Figure 8:
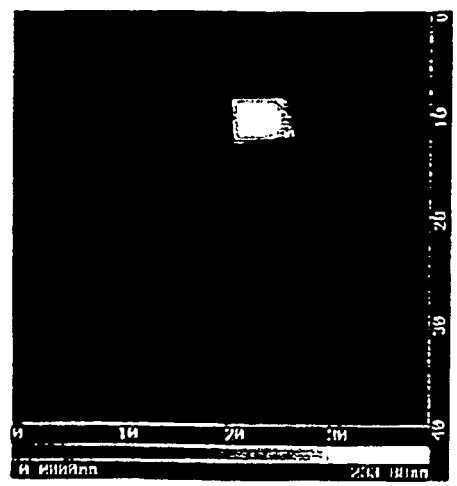
FIG. 8 is a microphotograph showing an example of actual forms of LPDs detected in the first embodiment, which were confirmed using the AFM.
Figure 9:
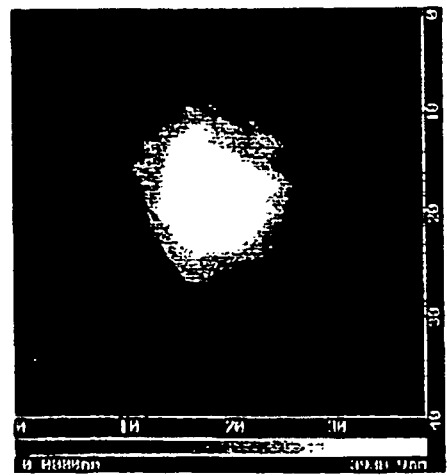
FIG. 9 is a microphotograph showing an example of actual forms of LPDs detected in the first embodiment, which were confirmed using the AFM.

In FIGS. 2–9, typical examples of microphotographs of the actual forms of the LPDs confirmed using the AFM are shown. In Table 3, in order to clarify correspondence to the LPDs shown in FIGS. 2–7, the Figure numbers are included in the AFM column. The LPD shown in FIG. 8 is an example of an LPD which should be classified as the division (B>160 nm and A<107 nm) in Table 1, while the LPD shown in FIG. 9 is an example of an LPD which should be classified as the division (Others) in Table 1.

In the method according to the Example, the LPDs could be accurately classified according to their forms (i.e. shapes) with a probability of at least 90% by a simple method using a laser surface inspection apparatus.

Comparative Example 1

Used laser surface inspection apparatus: SFS6220 (produced by TENCOR)
One light optic relative to one incidence
Used sample: 200 mm epitaxial silicon wafer
  Wafer crystal plane (100)
  Epitaxial film thickness 2.1 μm
LPDs of the sample epitaxial silicon wafer were detected using the above laser surface inspection apparatus.

Classification based on standard particle conversion size data of the LPDs using the laser surface inspection apparatus, and classification by a method wherein a high-intensity spotlight is irradiated in a darkroom and scatterers are detected by a visual check, were conducted. Actual forms of detected LPDs were confirmed using an AFM, and whether the classification was correct or wrong was judged. The results are shown in Table 4.

TABLE 4

| Laser surface inspection apparatus | Visual check | AFM |
|---|---|---|
| 0.1 μm > 10 LPDs | None | 10 SFs (3 μm-side square, L-shaped, U-shaped and linear) |
| 0.1–0.3 μm 5 LPDs | 3 SFs | 2 SFs (3 μm-side square), 1 pit of diameters 3.0 μm × 0.2 μm, 1 abnormal crystal growth, and 1 adherent particle |
| 0.3 μm < 3 LPDs | 3 extraneous substances | 2 non-epi-layer originated extraneous substances and 1 mound |

As is obvious from the results shown in Table 4, in the classification by a visual check, a detecting rate of LDPs as a precondition reached only 30% (6 LPDs/18 LPDs), which made clear that there was a problem before classification. And, among the detected LPDs, only 50% or so could be divided correctly. Thus, it was confirmed in the visual distinction by an inspector, that distinction was unstable, that it was difficult to deal with higher-level requirements in a future wafer inspection, and that probability that defects may escape the inspector's attention might become larger as wafers have larger diameters.

Example 2

Used laser surface inspection apparatus: SP-1 (produced by TENCOR)
Two light optics relative to one incidence
Used sample: 200 mm mirror-polished CZ silicon wafer
  Wafer crystal plane (100)
LPDs of the sample mirror-polished CZ silicon wafer were detected using the above laser surface inspection apparatus.

Data of coordinates and standard particle conversion sizes of the LPDs obtained from each of the two light optics were organized, and actual forms of the LPDs were presumed based on classification shown in Table 2. A portion of results of data processing is shown in Table 5.

TABLE 5

Detection results by laser surface inspection apparatus

| Low-angle light-receiving channel (nm) | High-angle light-receiving channel (nm) | Presumption | AFM | Results |
|---|---|---|---|---|
| Below detection limit | 112 | Scratch or s-pit | Scratch of length 3 μm (FIG. 10) | ○ |
| Below detection limit | 115 | Scratch or s-pit | Scratch | ○ |
| 98 | 142 | Scratch or s-pit | s-pit (FIG. 11) | ○ |
| 110 | 149 | Scratch or s-pit | s-pit | ○ |
| 86 | 132 | Scratch or s-pit | Scratch | ○ |
| 91 | Below detection limit | Grown-in defect in bulk | No unevenness observed | ○ |
| 88 | Below detection limit | Grown-in defect in bulk | No unevenness observed | ○ |
| 132 | 133 | Adherent particle | Adherent particle | ○ |
| 104 | 109 | Adherent particle | Adherent particle | ○ |

Then, on the basis of the coordinate data of the obtained LPDs, actual forms of the LPDs detected using the laser surface inspection apparatus were actually confirmed using an AFM, and whether the classification based on Table 2 was correct or wrong was judged. The results are also shown together in Table 5.

Figure 10:
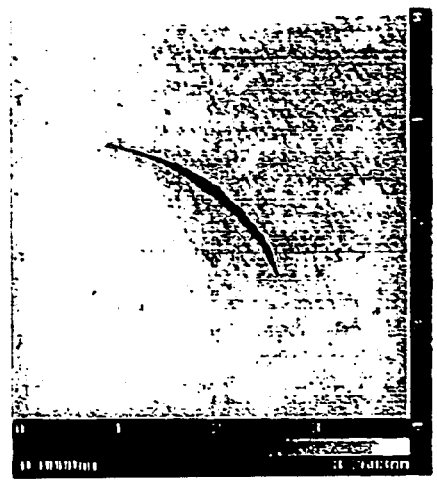
FIG. 10 is a microphotograph showing an example of actual forms of LPDs detected in a second embodiment, which were confirmed using an AFM.
Figure 11:
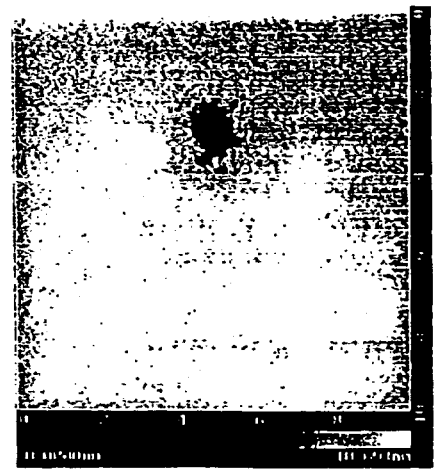
FIG. 11 is a microphotograph showing an example of actual forms of LPDs detected in the second embodiment, which were confirmed using the AFM.
Figure 13:
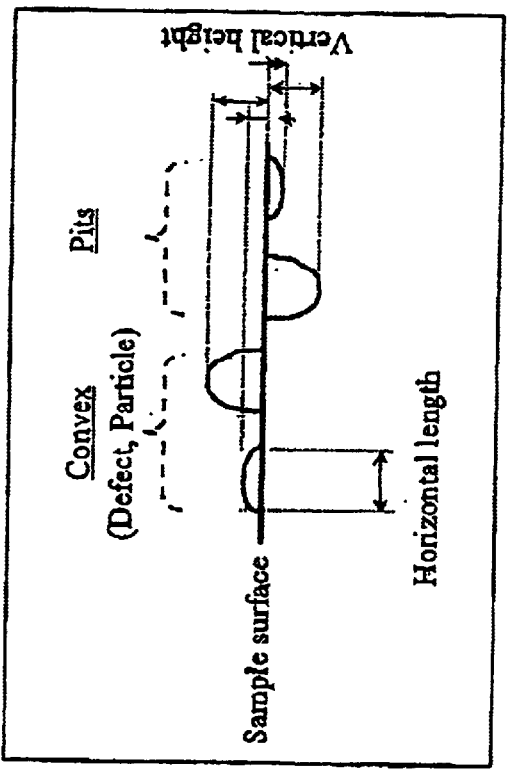
FIG. 13 depicts horizontal and vertical dimensions of occurrences in a semiconductor wafer.
Figure 12:
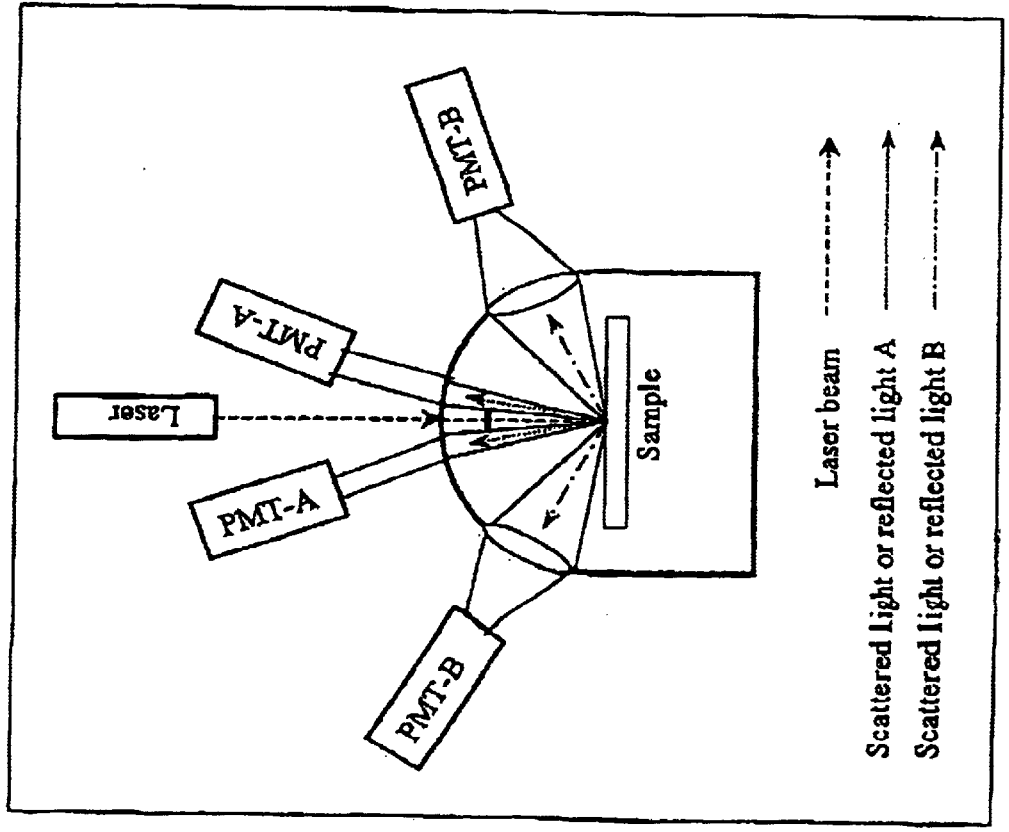
FIG. 12 schematically depicts performance of a method of the invention.

In FIGS. 10 and 11, typical examples of microphotographs of the actual forms of the LPDs confirmed using the AFM are shown. In Table 5, in order to clarify correspondence to the LPDs shown in FIGS. 10 and 11, the Figure numbers are included in the AFM column. In the method according to the Example, the LPDs could be accurately classified according to their forms (i.e. shapes) with a probability of at least 90% by a simple method using a laser surface inspection apparatus.

INDUSTRIAL APPLICABILITY

The instant invention can be utilized for dividing, to detect according to types of defects present on and near a semiconductor wafer surface, adherent particles and the like, which affect electrical properties such as dielectric breakdown strength of LSIs and the like manufactured using semiconductor wafers, so as to evaluate semiconductor wafer quality.

What is claimed is:

1. A method for inspecting a semiconductor wafer surface, comprising:

scanning a semiconductor wafer with a laser beam directed perpendicularly to said semiconductor wafer;

detecting at least one of scattered and reflected light from a surface of said semiconductor wafer by multiple light optics having different detecting angles, respectively, relative to said laser beam, wherein at least one of said multiple light optics is a high-angle light optic having a detecting angle that is from 5° to 20° relative to said laser beam and at least another of said multiple light optics is a low-angle light optic having a detecting angle that is from 25° to 75° relative to said laser beam; and determining a type and approximate shape of an occurrence associated with said semiconductor wafer based on a ratio of light intensities from said multiple light optics.

2. The method according to claim 1, wherein a laser surface inspection apparatus having at least two optics relative to one incidence is used to detect the at least one of scattered and reflected light.

3. The method according to claim 1, wherein said semiconductor wafer comprises an epitaxial semiconductor wafer.

4. The method according to claim 1, wherein the type and approximate shape of an occurrence associated with said semiconductor wafer is determined depending on a combination of A, B, and A/B, where light intensity from a high-angle light optic is A and light intensity from a low-angle light optic is B.

5. The method according to claim 1, wherein the type and approximate shape of an occurrence associated with said semiconductor wafer is determined depending on a combination of A, B, and A/B, where standard particle conversion size of a light point defect detected in a high-angle light optic is A and standard particle conversion size of a light point defect detected in a low-angle light optic is B.

6. The method according to claim 1, wherein the type and approximate shape of an occurrence associated with said semiconductor wafer is determined based upon the following table

| Relations between A and B or ranges | Actual types |
| --- | --- |
| A ≧ B × 1.13 | Stacking Fault |
| A < B × 1.13 | Non-epi-layer originated extraneous substance (adherent particle) |
| B < 90 nm and A > 107 nm | Micro-crystallographic-defect (hillock, shadow, dislocation) |
| B > 160 nm and A < 107 nm | Abnormal growth (large-pit, projection) |
| Others | Abnormal product | where standard particle conversion size of a light point defect detected in a high-angle light optic is A and standard particle conversion size of a light point defect detected in a low-angle light optic is B.

7. The method according to claim 1, wherein said semiconductor wafer comprises a mirror-finished semiconductor wafer.

8. The method according to claim 7, wherein the type and approximate shape of an occurrence associated with said semiconductor wafer is determined depending on a combination of A, B, and A/B, where light intensity from a high-angle light optic is A and light intensity from a low-angle light optic is B.

9. The method according to claim 7, wherein the type and approximate shape of an occurrence associated with said semiconductor wafer is determined depending on a combination of A, B, and A/B, where standard particle conversion size of a light point defect detected in a high-angle light optic is A and standard particle conversion size of a light point defect detected in a low-angle light optic is B.

10. The method according to claim 7, wherein the type and approximate shape of an occurrence associated with said semiconductor wafer is determined based upon the following table

| Relations between A and B or ranges | Actual types |
| --- | --- |
| A ≧ B × 1.13 or B < 90 nm and A > 107 nm | Scratch, flaw, and shallow pit |
| A < B × 1.13 | Adherent particle or COP |
| B ≧ 85 nm and A < 107 nm | Grown-in defect in bulk near surface | where standard particle conversion size of a light point defect detected in a high-angle light optic is A and standard particle conversion size of a light point defect detected in a low-angle light optic is B.

11. The method according to claim 1, wherein the type and approximate shape of an occurrence associated with said semiconductor wafer is determined based upon the following table

| Relations between A and B or ranges | Actual types |
| --- | --- |
| A ≧ B × 1.13 or B < 90 nm and A > 107 nm | Scratch, flaw, and shallow pit |
| A < B × 1.13 | Adherent particle or COP |
| B ≧ 85 nm and A < 107 nm | Grown-in defect in bulk near surface | where standard particle conversion size of a light point defect detected in a high-angle light optic is A and standard particle conversion size of a light point defect detected in a low-angle light optic is B.

12. A method for inspecting a semiconductor wafer surface, comprising:

scanning a semiconductor wafer with a laser beam directed perpendicularly to said semiconductor wafer;

detecting at least one of scattered and reflected light from a surface of said semiconductor wafer by multiple light optics having different detecting angles, respectively, relative to said laser beam, wherein at least one of said multiple light optics is a high-angle light optic having a detecting angle that is from 5° to 20° relative to said laser beam and at least another of said multiple light optics is a low-angle light optic having a detecting angle that is from 25° to 75° relative to said laser beam;

from a difference in standard particle conversion sizes of a light point defect based on a ratio of light intensities from said multiple light optics, calculating one of (i) a difference between a horizontal length and a vertical height of a light point defect present on a surface of said semiconductor wafer, and (ii) a difference between two orthogonal horizontal lengths of a light point defect present on a surface of said semiconductor wafer; and determining a type and approximate shape of an occurrence associated with said semiconductor wafer.

13. The method according to claim 12, wherein a laser surface inspection apparatus having at least two optics relative to one incidence is used to detect the at least one of scattered and reflected light.

14. The method according to claim 13, wherein said semiconductor wafer comprises an epitaxial semiconductor wafer.

15. The method according to claim 13, wherein the type and approximate shape of an occurrence associated with said semiconductor wafer is determined depending on a combination of A, B, and A/B, where light intensity from a high-angle light optic is A and light intensity from a low-angle light optic is B.

16. The method according to claim 13, wherein the type and approximate shape of an occurrence associated with said semiconductor wafer is determined depending on a combination of A, B, and A/B, where standard particle conversion size of a light point defect detected in a high-angle light optic is A and standard particle conversion size of a light point defect detected in a low-angle light optic is B.

17. The method according to claim 12, wherein said semiconductor wafer comprises an epitaxial semiconductor wafer.

18. The method according to claim 12, wherein the type and approximate shape of an occurrence associated with said semiconductor wafer is determined depending on a combination of A, B, and A/B, where light intensity from a high-angle light optic is A and light intensity from a low-angle light optic is B.

19. The method according to claim 12, wherein the type and approximate shape of an occurrence associated with said semiconductor wafer is determined depending on a combination of A, B, and A/B, where standard particle conversion size of a light point defect detected in a high-angle light optic is A and standard particle conversion size of a light point defect detected in a low-angle light optic is B.

20. The method according to claim 12, wherein the type and approximate shape of an occurrence associated with said semiconductor wafer is determined based upon the following table

| Relations between A and B or ranges | Actual types |
| --- | --- |
| A ≥ B × 1.13 | Stacking Fault |
| A < B × 1.13 | Non-epi-layer originated extraneous substance (adherent particle) |
| B < 90 nm and A > 107 nm | Micro-crystallographic-defect (hillock, shadow, dislocation) |
| B > 160 nm and A < 107 nm | Abnormal growth (large-pit, projection) |
| Others | Abnormal product | where standard particle conversion size of a light point defect detected in a high-angle light optic is A and standard particle conversion size of a light point defect detected in a low-angle light optic is B.

21. The method according to claim 12, wherein said semiconductor wafer comprises a mirror-finished semiconductor wafer.

22. The method according to claim 21, wherein the type and approximate shape of an occurrence associated with said semiconductor wafer is determined depending on a combination of A, B, and A/B, where light intensity from a high-angle light optic is A and light intensity from a low-angle light optic is B.

23. The method according to claim 21, wherein the type and approximate shape of an occurrence associated with said semiconductor wafer is determined depending on a combination of A, B, and A/B, where standard particle conversion size of a light point defect detected in a high-angle light optic is A and standard particle conversion size of a light point defect detected in a low-angle light optic is B.

24. The method according to claim 21, wherein the type and approximate shape of an occurrence associated with said semiconductor wafer is determined based upon the following table

| Relations between A and B or ranges | Actual types |
| --- | --- |
| A ≥ B × 1.13 or B < 90 nm and A > 107 nm | Scratch, flaw, and shallow pit |
| A < B × 1.13 | Adherent particle or COP |
| B ≥ 85 nm and A < 107 nm | Grown-in defect in bulk near surface | where standard particle conversion size of a light point defect detected in a high-angle light optic is A and standard particle conversion size of a light point defect detected in a low-angle light optic is B.

25. The method according to claim 12, wherein the type and approximate shape of an occurrence associated with said semiconductor wafer is determined based upon the following table

| Relations between A and B or ranges | Actual types |
| --- | --- |
| A ≥ B × 1.13 or B < 90 nm and A > 107 nm | Scratch, flaw, and shallow pit |
| A < B × 1.13 | Adherent particle or COP |
| B ≥ 85 nm and A < 107 nm | Grown-in defect in bulk near surface | where standard particle conversion size of a light point defect detected in a high-angle light optic is A and standard particle conversion size of a light point defect detected in a low-angle light optic is B.

* * * * *